(12) United States Patent
Joye et al.

(10) Patent No.: US 6,648,879 B2
(45) Date of Patent: Nov. 18, 2003

(54) SAFETY CRYOTHERAPY CATHETER

(75) Inventors: James Joye, Monte Sereno, CA (US); Keith Burger, San Francisco, CA (US); Michael Fourkas, Menlo Park, CA (US); Timothy Holland, Los Gatos, CA (US)

(73) Assignee: Cryovascular Systems, Inc., Los Gatos, CA (US)

( * ) Notice: Subject to any disclaimer, the term of this patent is extended or adjusted under 35 U.S.C. 154(b) by 0 days.

(21) Appl. No.: 09/953,464

(22) Filed: Sep. 14, 2001

(65) Prior Publication Data
US 2002/0045894 A1 Apr. 18, 2002

Related U.S. Application Data

(63) Continuation-in-part of application No. 09/619,583, filed on Jul. 19, 2000, which is a continuation-in-part of application No. 09/268,205, filed on Mar. 15, 1999, now Pat. No. 6,432,102, and a continuation-in-part of application No. 09/510,903, filed on Feb. 23, 2000, now Pat. No. 6,428,534.
(60) Provisional application No. 60/121,638, filed on Feb. 24, 1999.

(51) Int. Cl.[7] ............................................... A61B 18/18
(52) U.S. Cl. ......................................... 606/21; 128/898
(58) Field of Search .......................... 606/20–26, 192, 606/194; 607/104, 105, 106

(56) References Cited

U.S. PATENT DOCUMENTS

| | | | |
|---|---|---|---|
| 3,125,096 A | 3/1964 | Antiles et al. | |
| 3,630,203 A | 12/1971 | Sellinger et al. | |
| 3,901,241 A | 8/1975 | Allen, Jr. | |
| 4,336,691 A | 6/1982 | Burstein et al. | |
| 4,754,752 A | 7/1988 | Ginsburg et al. | |
| 5,019,075 A | 5/1991 | Spears et al. | |
| 5,041,089 A | 8/1991 | Mueller et al. | |
| 5,078,713 A | 1/1992 | Varney | |
| 5,092,841 A | 3/1992 | Spears | |
| 5,106,360 A | 4/1992 | Ishiwara et al. | |
| 5,117,870 A | 6/1992 | Goodale et al. | |
| 5,147,355 A | 9/1992 | Friedman et al. | |
| 5,151,100 A | 9/1992 | Abele et al. | |

(List continued on next page.)

FOREIGN PATENT DOCUMENTS

| | | |
|---|---|---|
| WO | WO 91/05528 | 5/1991 |
| WO | WO 98/38934 | 9/1998 |
| WO | WO 98/52479 A1 | 11/1998 |
| WO | WO 00/42931 | 7/2000 |
| WO | WO 02/04042 A2 | 1/2002 |
| WO | WO 02/07625 A2 | 1/2002 |
| WO | WO 02/38091 A1 | 5/2002 |

OTHER PUBLICATIONS

CMS Website Information "Cryomedical Science Introduces Cryolite®" http://www.cryomedical.com/R&D/cryolite.htm (Nov. 22, 1998), 3 pages total.

(List continued on next page.)

*Primary Examiner*—Roy D. Gibson
(74) *Attorney, Agent, or Firm*—Townsend and Townsend & Crew LLP; Mark D. Barrish, Esq.

(57) ABSTRACT

Improved devices, systems, and methods for inhibiting hyperplasia in blood vessels provide controlled and safe cryotherapy treatment of a target portion within a body lumen of a patient. One embodiment of the cryotherapy catheter comprises a catheter body having a proximal end and a distal end with a cooling fluid supply lumen and an exhaust lumen extending therebetween. A first balloon is disposed near the distal end of the catheter body in fluid communication with the supply and exhaust lumens. A second balloon is disposed over the first balloon with a barrier therebetween.

35 Claims, 8 Drawing Sheets

U.S. PATENT DOCUMENTS

| | | | |
|---|---|---|---|
| 5,190,539 | A | 3/1993 | Fletcher et al. |
| 5,191,883 | A | 3/1993 | Lennox et al. |
| 5,196,024 | A | 3/1993 | Barath |
| 5,275,595 | A | 1/1994 | Dobak, III |
| 5,383,853 | A | 1/1995 | Lennox et al. |
| 5,383,855 | A * | 1/1995 | Nicholson et al. ..... 604/100.03 |
| 5,417,653 | A * | 5/1995 | Sahota et al. ................. 604/20 |
| 5,458,612 | A | 10/1995 | Chin |
| 5,486,208 | A | 1/1996 | Ginsburg |
| 5,501,681 | A | 3/1996 | Neuwirth et al. |
| 5,545,195 | A | 8/1996 | Lennox et al. |
| 5,617,739 | A | 4/1997 | Little |
| 5,644,502 | A | 7/1997 | Little |
| 5,667,521 | A | 9/1997 | Keown |
| 5,733,280 | A | 3/1998 | Avitall |
| 5,814,040 | A | 9/1998 | Nelson et al. |
| 5,846,235 | A | 12/1998 | Pasricha et al. |
| 5,868,735 | A | 2/1999 | Lafontaine |
| 5,971,979 | A | 10/1999 | Joye et al. |
| 6,027,499 | A | 2/2000 | Johnston et al. |
| 6,290,696 | B1 | 9/2001 | Lafontaine |
| 6,379,378 | B1 | 4/2002 | Werneth et al. |
| 6,419,643 | B1 * | 7/2002 | Shimada et al. ............ 600/585 |

OTHER PUBLICATIONS

CMS Website Information "Cell Suicide Following Cryosurgery" http://www.cryomedical.com/R&D/apoptosi.htm (Mar. 8, 1999), 3 pages total.

U.S. Patent Application No. 09/203,011 filed on Dec. 1, 1998 entitled: *Apparatus and Method for Cryogenic Inhibition of Hyperplasia,* Inventor(s): James Joye et al. (Atty. Docket No. 18468–000110US).

U.S. Patent Application No. 09/344,177 filed on Jun. 24, 1999 entitled: *Cryosurgical Catheter Inhibition of Hyperplasia,* Inventor(s): James Joye et al. (Atty. Docket No. 18468–000120US).

U.S. Provisional Patent Application No. 60/121,638 filed on Feb. 24, 1999 entitled: *Cryogenic Angioplasty Catheter,* Inventor(s): James Joye et al. (Atty. Docket No. 18468–000400US).

U.S. Provisional Patent Application No. 60/121,637 filed on Feb. 24, 1999 entitled: *Cryogenic Angioplasty Catheter,* Inventor(s): James Joye et al. (Atty. Docket No. 18468–000500US).

U.S. Patent Application No. 09/268,205 filed Mar. 15, 1999 entitled: *Cryosurgical Fluid Supply,* Inventor(s): James Joye et al. (Atty. Docket No. 18468–000600US).

Meinhard Nebulizer, "The Meinhard® Concentric Glass Nebulizer," http://www.meinhard.com/product3.htm. pp. 1–2.

* cited by examiner

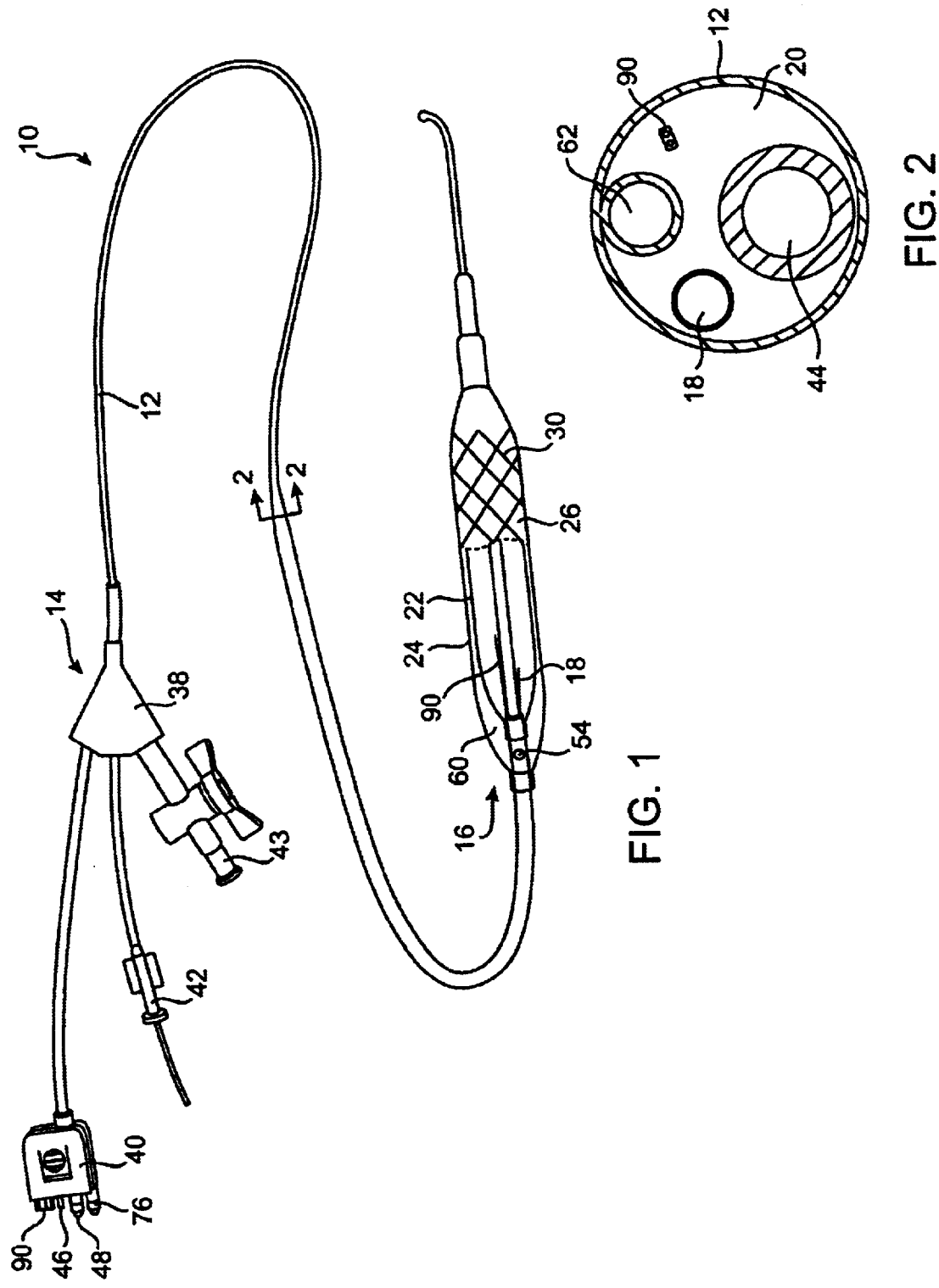

SAFETY CRYOTHERAPY CATHETER

CROSS-REFERENCES TO RELATED APPLICATIONS

This application is a continuation-in-part of co-pending U.S. patent application Ser. No. 09/619,583, filed Jul. 19, 2000, which is a continuation-in-part of co-pending U.S. patent application Ser. No. 09/268,205, filed Mar. 15, 1999; and of co-pending U.S. patent application Ser. No. 09/510,903, filed on Feb. 23, 2000, which is a continuation-in-part of and claims priority from U.S. Provisional Patent Application No. 60/121,638, filed on Feb. 24, 1999. The full disclosures of each of the above references are incorporated herein by reference.

BACKGROUND OF THE INVENTION

1. Field of the Invention

The present invention relates generally to apparatus and methods for inhibiting restenosis in blood vessels following angioplasty or other intravascular procedures for treating atherosclerosis and other diseases of the vasculature. More particularly, the present invention provides improved apparatus and methods for cryogenically treating a lesion within a patient's vasculature to inhibit hyperplasia (which often occurs after intravascular procedures).

A number of percutaneous intravascular procedures have been developed for treating atherosclerotic disease in a patient's vasculature. The most successful of these treatments is percutaneous transluminal angioplasty (PTA). PTA employs a catheter having an expansible distal end, usually in the form of an inflatable balloon, to dilate a stenotic region in the vasculature to restore adequate blood flow beyond the stenosis. Other procedures for opening stenotic regions include directional arthrectomy, rotational arthrectomy, laser angioplasty, stents and the like. While these procedures, particularly PTA and stenting, have gained wide acceptance, they continue to suffer from the subsequent occurrence of restenosis.

Restenosis refers to the re-narrowing of an artery following an initially successful angioplasty or other primary treatment. Restenosis typically occurs within weeks or months of the primary procedure, and may affect up to 50% of all angioplasty patients to some extent. Restenosis results at least in part from smooth muscle cell proliferation in response to the injury caused by the primary treatment. This cell proliferation is referred to as "hyperplasia." Blood vessels in which significant restenosis occurs will typically require further treatment.

A number of strategies have been proposed to treat hyperplasia and reduce restenosis. Previously proposed strategies include prolonged balloon inflation, treatment of the blood vessel with a heated balloon, treatment of the blood vessel with radiation, the administration of anti-thrombotic drugs following the primary treatment, stenting of the region following the primary treatment, and the like. While these proposals have enjoyed varying levels of success, no one of these procedures is proven to be entirely successful in avoiding all occurrences of restenosis and hyperplasia.

It has recently been proposed to prevent or slow reclosure of a lesion following angioplasty by remodeling the lesion using a combination of dilation and cryogenic cooling. Co-pending U.S. patent application Ser. No. 09/203,011, filed Dec. 1, 1998 (Attorney Docket No. 18468-000110), the full disclosure of which is incorporated herein by reference, describes an exemplary structure and method for inhibiting restenosis using a cryogenically cooled balloon. While these proposals show great promise for endovascular use, the described structures and methods for carrying out endovascular cryogenic cooling would benefit from still further improvements. In particular, it can be challenging to safely and reproducibly effect the desired controlled cooling. For example, many potential cryogenic fluids, such as liquid nitrous oxide, exhibit high levels of heat transfer. This is problematic as high cooling temperatures may kill the cooled cells (cell necrosis) rather than provoking the desired antiproliferative effect of endoluminal cryotherapy. Additionally, the use of nitrous oxide as a balloon inflation media often results in limited visibility of the cooling balloon, especially smaller sized balloons, making it difficult to properly visualize the inflated cooling balloon within a lesion site. Further, improved safety measures that would prevent against cooling balloon failures and/or minimize leakage of any cryogenic fluids into the blood stream would be beneficial. Moreover, cryogenic systems having low profiles and enhanced performance characteristics would be advantageous.

For these reasons, it would be desirable to provide improved devices, systems, and methods for treatment of restenosis and hyperplasia in blood vessels. It would be particularly desirable if these improved devices, systems, and methods were capable of delivering treatment in a very controlled and safe manner so as to avoid overcooling and/or injury to adjacent tissue. These devices, systems, and methods should ideally also inhibit hyperplasia and/or neoplasia in the target tissue with minimum side effects. At least some of these objectives will be met by the invention described herein.

2. Description of the Background Art

A cryoplasty device and method are described in WO 98/38934. Balloon catheters for intravascular cooling or heating a patient are described in U.S. Pat. No. 5,486,208 and WO 91/05528. A cryosurgical probe with an inflatable bladder for performing intrauterine ablation is described in U.S. Pat. No. 5,501,681. Cryosurgical probes relying on Joule-Thomson cooling are described in U.S. Pat. Nos. 5,275,595; 5,190,539; 5,147,355; 5,078,713; and 3,901,241. Catheters with heated balloons for post-angioplasty and other treatments are described in U.S. Pat. Nos. 5,196,024; 5,191,883; 5,151,100; 5,106,360; 5,092,841; 5,041,089; 5,019,075; and 4,754,752. Cryogenic fluid sources are described in U.S. Pat. Nos. 5,644,502; 5,617,739; and 4,336,691. A body cooling apparatus is described in U.S. Pat. No. 3,125,096. Rapid exchange catheters are described in U.S. Pat. Nos. 5,383,853 and 5,667,521. The following U.S. patents may also be relevant to the present invention: U.S. Pat. Nos. 5,458,612; 5,545,195; and 5,733,280.

The fall disclosures of each of the above references are incorporated herein by reference.

BRIEF SUMMARY OF THE INVENTION

The present invention provides improved devices, system, and methods for inhibiting hyperplasia in blood vessels. The blood vessels will often be treated for atherosclerotic or other diseases by balloon angioplasty, arthrectomy, rotational arthrectomy, laser angioplasty, stenting, or another primary treatment procedure. Inhibition of excessive cell growth is desirable when such treatments are employed so as to reduce and/or eliminate any associated hyperplasia and to maintain the patency of a body lumen. The present invention allows for cryotherapy treatment of a target portion within the body lumen of a patient in a very controlled and safe manner, particularly when using fluid capable of cooling tissues below a target temperature range.

In a first aspect, the invention provides a cryotherapy catheter comprising a catheter body having a proximal end and a distal end with a cooling fluid supply lumen and an exhaust lumen extending therebetween. A first balloon is disposed near the distal end of the catheter body in fluid communication with the supply and exhaust lumens. A second balloon is disposed over the first balloon with a barrier, typically a thermal barrier, therebetween.

Treatment according to this first aspect of the present invention can be effected by positioning the first balloon within the blood vessel adjacent a target portion. The "target portion" will often be a length within the blood vessel which is at risk of hyperplasia, typically as a result of balloon angioplasty (or some other treatment). Cryogenic cooling fluid is introduced into the first balloon (in which it often vaporizes) and exhausted. The second balloon expands to radially engage the vessel wall. The target portion is cooled to a temperature which is sufficiently low for a time which is sufficiently long to inhibit excessive cell proliferation. Heat transfer will be inhibited between the first and second balloons by the thermal barrier so as to limit cooling of the target portion. The inhibited cooling treatment will be directed at all or a portion of a circumferential surface of the body lumen, and will preferably result in cell growth inhibition, but not necessarily in significant cell necrosis. Particularly in the treatment of arteries before, during, and/or following balloon angioplasty, cell necrosis may be undesirable if it increases the hyperplastic response. Thus, the present invention will cool target tissue to a limited cooling temperatures to slow or stop cell proliferation.

In some embodiments, the barrier may comprise a separation or gap maintained between the balloons by a polyester layer. The polyester layer typically comprises a woven, braided, helically wound, or knotted polyester material. The polyester layer may be puncture resistant so as to provide further protection against any leakage of fluid from the first balloon. The polyester material may additionally help retain balloon folds of the first and/or second balloons after they are expanded so that the balloons may be more easily drawn back after a treatment procedure. The barrier may alternatively comprise a separation maintained between the balloons by a fluid layer. The fluid layer may comprise at least one liquid selected from the group consisting of propylene glycol, propylene glycol 200, propylene glycol 300, propylene glycol 400, propylene glycol 600, glycerin, ethyl alcohol 75%, ethyl alcohol 95%, dimethyl sulfoxide, glyceryl formal, N-methyl-2-pyrrolidone, tetrahydrofurfuryl, dimethyl acetamide, and monthiol glycerol.

A radiopaque marker may be disposed on or within the barrier for proper positioning of the cryotherapy balloons within the target portion of the blood vessel under fluoroscopy. For example, the radiopaque marker may be disposed on the polyester layer in a stent-like pattern or radiopaque contrast agent may be disposed within the fluid layer. The radiopaque marker is preferably a non-toxic contrast medium, such as, gold, and preferably tungsten and does not significantly alter the thermal insulation properties of the barrier. Areas of the barrier adjacent the balloon folds may be free of any radiopaque marking so as to further minimize the balloon profile. The radiopaque marker may also be electrically conductive so as to monitor any leaks in the separation between the balloons or to measure an interface temperature between the balloons.

Suitable cryogenic fluids will preferably be non-toxic and include liquid nitrous oxide, liquid carbon dioxide, cooled saline and the like. The balloons are preferably inelastic and have a length of at least 1 cm each, more preferably in the range from 2 cm to 5 cm each in a coronary artery and 2 cm to 10 cm each in a periphery artery. The balloons will have diameters in the range from 2 mm to 5 mm each in a coronary artery and 2 mm to 10 mm each in a periphery artery. Generally, the temperature of the outer surface of the first balloon will be in a range from about 0° C. to about −50° C. and the temperature of the outer surface of the second balloon will be in a range from about −3° C. to about −15° C. This will provide a treatment temperature in a range from about −3° C. to about −15° C. The tissue is typically maintained at the desired temperature for a time period in the range from about 1 to 60 seconds, preferably being from 20 to 40 seconds. Hyperplasia inhibiting efficacy may be enhanced by repeating cooling in cycles, typically with from about 1 to 3 cycles, with the cycles being repeated at a rate of about one cycle every 60 seconds.

In another aspect of the present invention, a cryotherapy system comprises an elongate body having a proximal end and a distal end with a fluid supply, an exhaust lumen, and a plurality of vacuum lumens extending therebetween. A first balloon defines a volume in fluid communication with the supply and exhaust lumens. A fluid shutoff couples a cryogenic fluid supply with the supply lumen. A second balloon is disposed over the first balloon with a vacuum space therebetween. The vacuum space is coupled to the fluid shutoff by the plurality of vacuum lumens. The fluid shutoff inhibits flow of cryogenic fluid into the first balloon in response to a change in at least one of the vacuum lumens and/or in response to a change in the vacuum space. Advantageously, the cryotherapy system can monitor the integrity of both the catheter body and the balloons during cooling to ensure that there are no breaches in the catheter shaft or the balloons. Further, in the event of a failure, the fluid shutoff can prevent the delivery of additional cryogenic fluid into the supply lumen and the second balloon can act to contain any cryogenic fluid that may have escaped the first balloon.

The fluid shutoff typically comprises a vacuum switch connected to a shutoff valve by a circuit, the circuit being powered by a battery. The switch may remain closed only when a predetermined level of vacuum is detected. The closed switch allows the shutoff valve (in fluid communication with the cryogenic fluid supply) to be open. Alternatively, the circuit may be arranged so that the switch is open only when the predetermined vacuum is present, with the shutoff valve being open when the switch is open. The vacuum is reduced when there is a breach in the catheter body, allowing cryogenic fluid or blood to enter at least one vacuum lumen, the first balloon is punctured, allowing cryogenic fluid to enter the vacuum space, or the second balloon is punctured, allowing blood to enter the vacuum space. The vacuum may be provided by a positive displacement pump, such as a syringe, coupled to the vacuum space by the plurality of vacuum lumens. A valve, such as a stopcock, may be disposed between the syringe and the vacuum lumens so as to isolate a relatively large syringe volume from a relatively small vacuum volume. This in turn allows for increased sensitivity of small fluid leaks as the detection of changes in the vacuum as small as 0.2 mL may be monitored.

The system may further comprise a hypsometer with a thermocouple, pressure transducer, capillary tube, thermistor, or the like, coupled to the first balloon to determine a temperature and/or pressure of fluid in the first balloon. An indicator, such as a warning light or audio signal, may additionally be coupled to the thermocouple to provide a signal to an operator of the system when the first balloon temperature is above 0° C. As cryoplasty often results in adhesion of the cooling balloon to the vessel wall during treatment, an indicator allows an operator to know when to safely remove the cooling balloon at a safe temperature following treatment so that any potential tearing of the vessel resulting from a frozen cooling balloon is minimized.

In yet another aspect, the present invention provides a cryotherapy catheter comprising a catheter body having a proximal end and distal end with a cooling fluid supply lumen and an exhaust lumen extending therebetween. A first balloon is disposed at the distal end of the catheter body, the first balloon having an inner surface in fluid communication with the supply and exhaust lumens. A second balloon is disposed over the first balloon, wherein proximal and distal balloon stems of the first and second balloon are staggered along the distal end of the catheter body. The balloons stems or bond joints are staggered to provide a lower balloon folding profile and to allow positioning of a vacuum port between the proximal balloon stems of the first and second balloons. The balloon stems of the first and second balloons will be staggered from each other by a distance of 5 mm or less, preferably from about 2 mm to about 3 mm. The cryotherapy catheter may further comprise at least one rupture disk molded into a proximal or distal balloon stem of the first balloon. In some instances, cryotherapy balloons may fail or burst on inner bond joints in a peel mode. As such, it is desirable to mold rupture discs into the balloons stems to preclude such bond joint failures. Rupture discs will reduce a stem thickness to about 0.0005 inches or less.

In another aspect of the present invention, a cryotherapy system comprises a catheter body having a proximal end and a distal end with a cooling fluid supply lumen and an exhaust lumen extending therebetween. A balloon is disposed at the distal end of the catheter body, the first balloon having an inner surface in fluid communication with the supply lumen and exhaust lumen. A pressure transducer is coupled to the catheter body so as to measure gas pulse pressure therein. A fluid shutoff couples a cryogenic cooling fluid supply with the supply lumen. The pressure transducer is coupled to the fluid shutoff so as to inhibit flow of cryogenic fluid into the first balloon if the pressure measured by the pressure transducer is below 60 psi or above 80 psi. Alternatively, the fluid shutoff may inhibit flow of cryogenic fluid into the first balloon if a pressure decay measured by the pressure transducer is greater than 5 psi. Hence, the present system incorporates a pretreatment test to monitor containment of the system (i.e. catheter body, supply lumen, guidewire lumen, balloons) prior to any treatment procedures. In the case of a breach in the system, the fluid shutoff will inhibit any flow of cryogenic fluid into the catheter. The pretreatment test may be effected by introducing a pulse of gas, typically nitrous oxide, into a balloon with a supply lumen and exhausting the gas. Containment of the supply lumen, balloon, guidewire lumen, and catheter body are monitored by measuring a gas pulse pressure. Flow of cryogenic fluid is inhibited into the balloon if the measured pressure is below a threshold pressure.

In still another aspect of the present invention, methods for enhancing cryogenic cooling fluid flow rates in a cryotherapy system are provided. The method comprises introducing a cryogenic cooling fluid into a balloon with a supply lumen. The balloon is flooded so that at least some of the cooling fluid is exhausted in the balloon and at least some of the cooling fluid overflows into an exhaust lumen. The supply lumen and cryogenic fluid therein are cooled so as to enhance a flow rate of the cryogenic cooling fluid. Enhanced flow rates achieved from flooding the cryotherapy balloon also allow the supply lumen diameter to be reduced to a range from about 0.004 inches to about 0.012 inches. Moreover, the cryotherapy system may be less dependent on fluid canister pressure as enhanced flow rates compensate for lower cryogenic cooling fluid canister pressurizations at a range from about 850 psi to about 600 psi.

A further understanding of the nature and advantages of the present invention will become apparent by reference to the remaining portions of the specification and drawings.

BRIEF DESCRIPTION OF THE DRAWINGS

FIG. 1 illustrates an exemplary cryotherapy catheter constructed in accordance with the principles of the present invention.

FIG. 2 is a cross-sectional view of the cryotherapy catheter taken along lines 2—2 in FIG. 1.

DETAILED DESCRIPTION OF THE INVENTION

Figure 3:
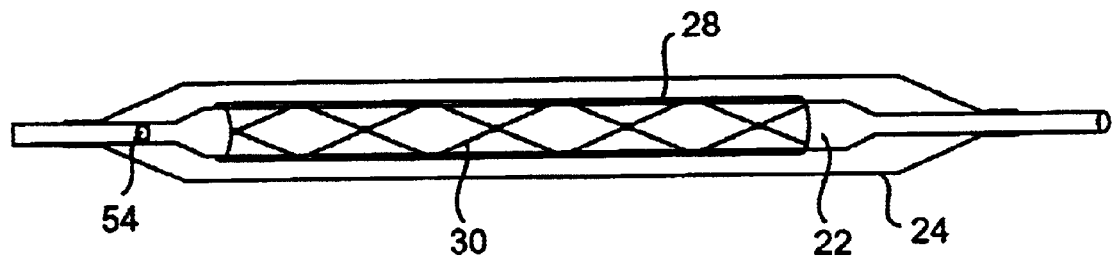
FIG. 3 illustrates an exploded view of the distal end of the cryotherapy catheter of FIG. 1.

The present invention provides improved cryotherapy devices, systems, and methods for inhibiting hyperplasia in blood vessels. An exemplary cryotherapy catheter 10 constructed in accordance with the principles of the present invention is illustrated in FIGS. 1 and 2. The catheter 10 comprises a catheter body 12 having a proximal end 14 and a distal end 16 with a cooling fluid supply lumen 18 and an exhaust lumen 20 extending therebetween. A first balloon 22 is disposed near the distal end 16 of the catheter body 12 in fluid communication with the supply and exhaust lumens. A second balloon is disposed 24 over the first balloon 22 with a barrier 26, typically a thermal barrier, therebetween. It will be appreciated that the following depictions are for illustration purposes only and does not necessarily reflect the actual shape, size, or dimensions of the cryotherapy catheter 10. This applies to all depictions hereinafter.

The balloons 22, 24 may be an integral extension of the catheter body 12, but such a structure is not required by the present invention. The balloons 22, 24 could be formed from the same or a different material as the catheter body 12 and, in the latter case, attached to the distal end 16 of the catheter body 12 by suitable adhesives, heat welding, or the like. The catheter body 12 may be formed from conventional materials, such as polyethylenes, polyimides, nylons, polyesters, and copolymers and derivatives thereof. The balloons 22, 24 may also be formed from conventional materials used for angioplasty, preferably being inelastic, such as nylon, polyethylene terephthalate (PET), or polyethylene, elastic, such as urethane, latex, or silicone, or other medical grade material suitable for constructing a strong non-distensible balloon. Additionally, balloons 22 and 24 could be formed from different material to provide improved protection. For example, the first balloon 22 could be formed from PET to provide strength while the second balloon 24 could be formed from polyethylene to provide durability. The balloons 22, 24 have a length of at least 1 cm each, more preferably in the range from 2 cm to 5 cm each in a coronary artery and 2 cm to 10 cm each in a periphery artery. The balloons 22, 24 will have diameters in the range from 2 mm to 5 mm each in a coronary artery and 2 mm to 10 mm each in a periphery artery.

The thermal barrier 26 may comprise a separation or gap maintained between the balloons 22, 24 by a polyester layer 28, as shown in FIG. 3. The polyester layer 28 typically comprises a woven, braided, helically wound, or knotted polyester material (e.g., Saatifil Polyester PES 38/31 M sold commercially by SaatiTech located in Somers, N.Y.) which may be affixed to the first balloon 22 by adhesion bonding, heat welding, fasteners, or the like. The polyester layer 28 may be puncture resistant so as to provide further protection against any leakage of fluid from the first balloon 22. The polyester material 28 may additionally help retain balloon folds of the first and/or second balloons 22, 24 after they are expanded so that the balloons may be more easily drawn back after a treatment procedure.

Figure 4:
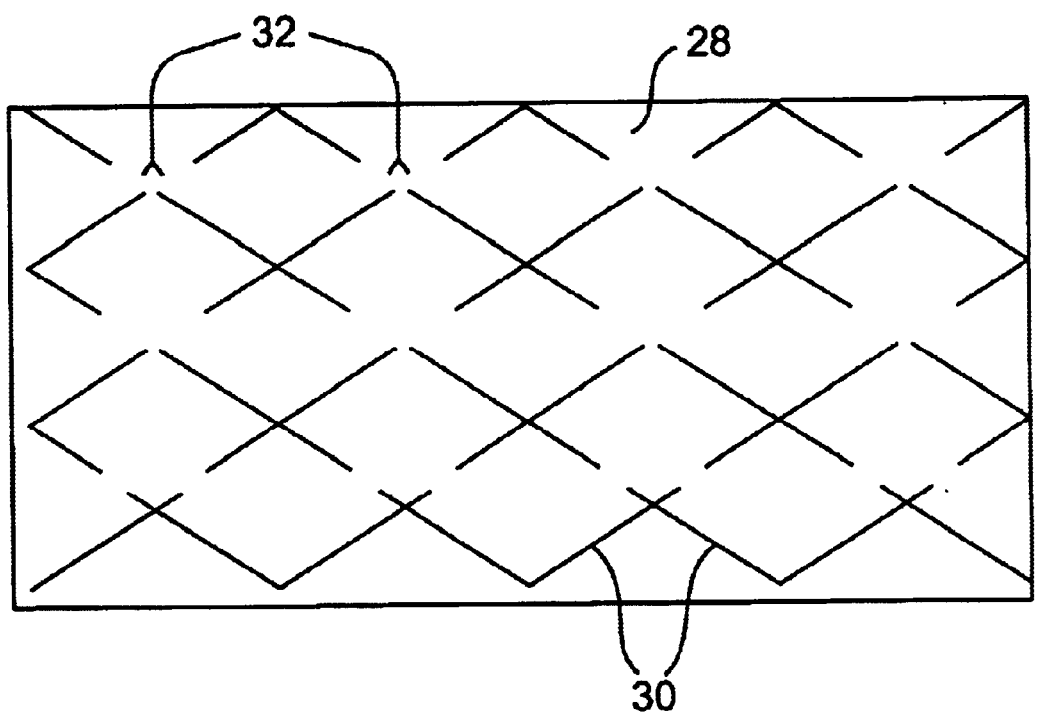
FIG. 4 illustrates a barrier having a radiopaque marking.

A radiopaque marker 30 may be disposed on the polyester layer 28 for proper positioning of the cryotherapy balloons 22, 24 within the target portion of the blood vessel under fluoroscopy. For example, the radiopaque marker 30 may be disposed on the polyester layer 28 in a stent-like pattern as depicted in FIG. 4. The radiopaque marker 30 is preferably a non-toxic contrast medium, such as, gold, and preferably tungsten and does not significantly alter the thermal insulation properties of the barrier. The marker 30 may be incorporated into an ink and printed onto the polyester layer itself. Areas of the polyester layer adjacent the balloon folds 32 may be free of any radiopaque marking so as to further minimize the balloon profile. The radiopaque marker 30 may also be electrically conductive so as to monitor any leaks in the separation between the balloons 22, 24.

Figure 5:
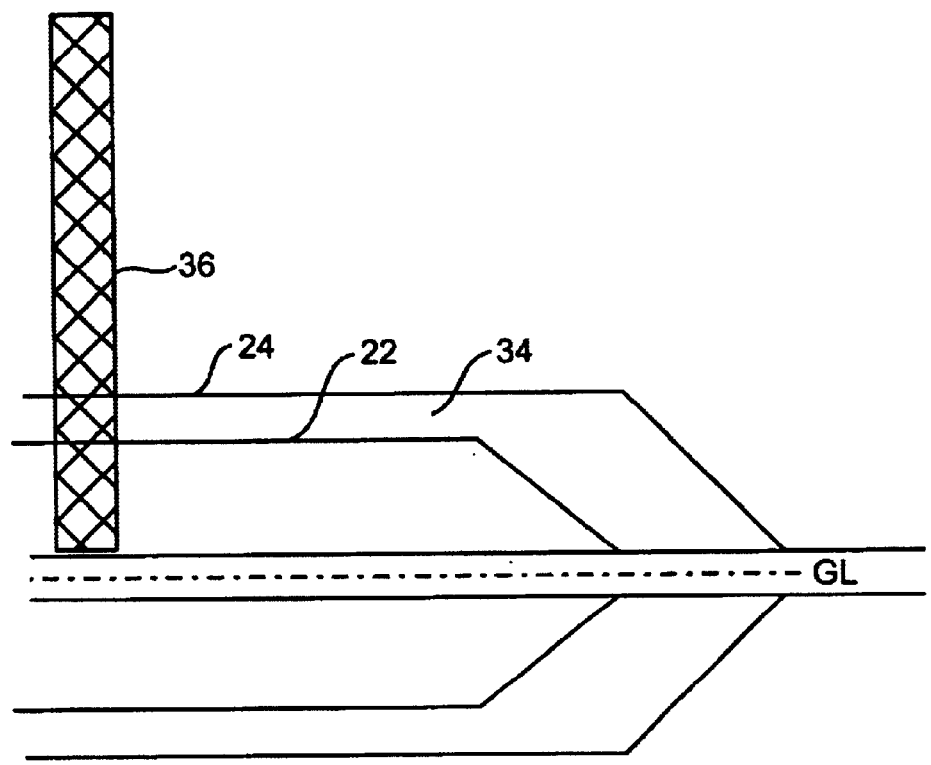
FIG. 5 illustrates a cross-sectional view of a distal end of a cryotherapy catheter with a fluid layer barrier.
Figure 6:
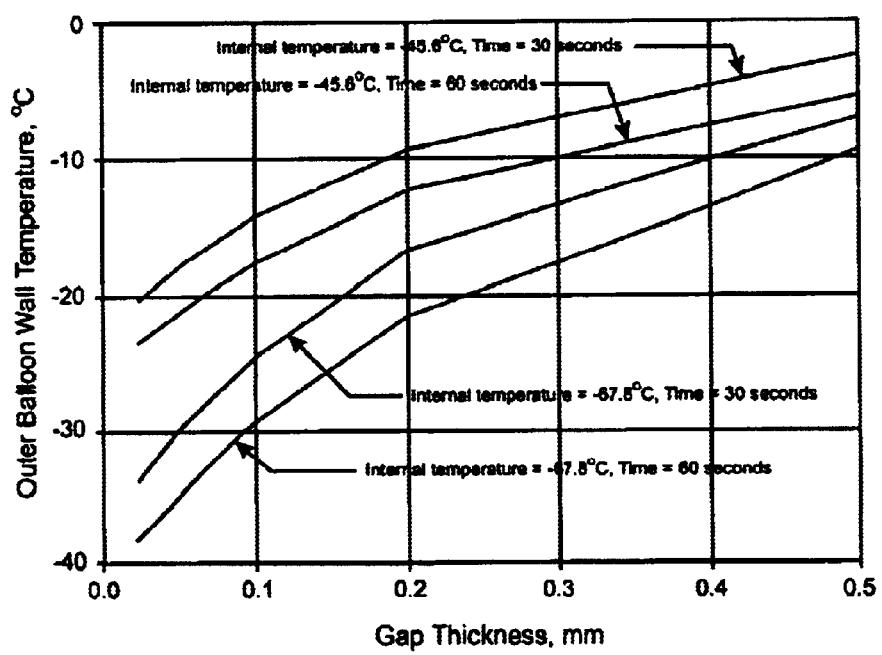
FIG. 6 is a graphical representation of the thermal characteristics of the fluid layer of FIG. 5.

Referring now to FIGS. 5 and 6, the thermal barrier 26 may alternatively comprise a separation maintained between the balloons by a fluid layer 34. The fluid will be chosen dependent on its specific thermal properties (e.g., predetermined phase change temperature), viscosity effects, miscibility with a radiopaque contrast agent, and like characteristics. The fluid layer 34 will generally comprise at least one liquid selected from the group consisting of propylene glycol, propylene glycol 200, propylene glycol 300, propylene glycol 400, propylene glycol 600, glycerin, ethyl alcohol 75%, ethyl alcohol 95%, dimethyl sulfoxide, glyceryl formal, N-methyl-2-pyrrolidose, tetrahydrofurfuryl, dimethyl acetamide, and monthiol glycerol. The liquid will generally be diluted with an aqueous solution, such as saline, dextrose 5%, or lactated Ringer's® solution. The gap thickness maintained by the fluid layer 34 depends on several criteria, such as, the pressure or temperature within the first balloon, the desired surface temperature of the second balloon, and the thermal transport properties of the fluid within the gap. Typically, the gap thickness maintained between the balloons 22, 24 by the fluid layer 34 will be in a range from about 0.1 mm to about 0.4 mm, preferably from about 0.25 mm to about 0.3 mm. FIG. 6 illustrates thermal characteristics for a particular cross section 36 of the cryotherapy catheter. This graphical representation shows that a second balloon 24 wall temperature of −3° C. to −15° C. (which will provide the desired treatment temperature of −3° C. to −15° C.) can be achieved for several combinations of internal temperature, gap thickness of the fluid layer, and cooling duration.

Hubs 38 and 40 are secured to the proximal end 14 of the catheter body 12. Hub 38 provides a port 42 for a guidewire which extends through a guidewire lumen 44 in the catheter body 12. Typically, the guidewire lumen 44 will extend through the exhaust lumen 20, as shown in FIG. 2. The guidewire lumen 44 may also extend axially outside the exhaust lumen 20 to minimize the occurrence of cryogenic fluid entering the blood stream via the guidewire lumen 44. Optionally, the guidewire lumen 44 may extend outside the inner surface of the first balloon 22 or the guidewire lumen 44 may allow for a guidewire to extend outside both balloons 22, 24. Hub 38 further provides a balloon deflation port 43 which allows final deflation of the balloon after a treatment procedure. Hub 40 provides a port 46 for connecting a cryogenic fluid source to the fluid supply lumen 18 which in turn is in fluid communication with the inner surface of the first balloon 22. Hub 40 further provides a port 48 for exhausting the cryogenic fluid which travels from balloon 22 in a proximal direction through the exhaust lumen 20.

Figure 7:
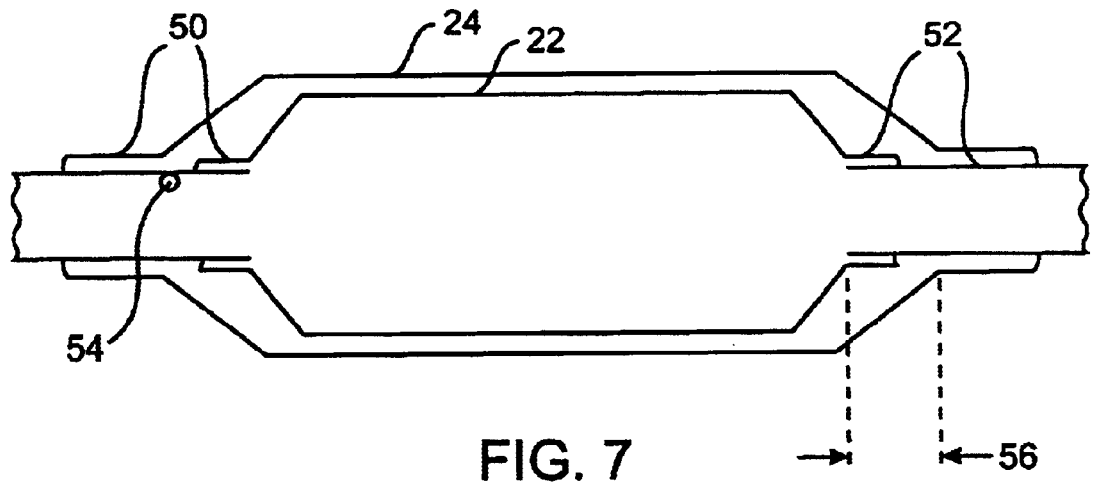
FIG. 7 illustrates an exploded view of a distal end of a cryotherapy catheter with staggered balloon stems.
Figure 8:
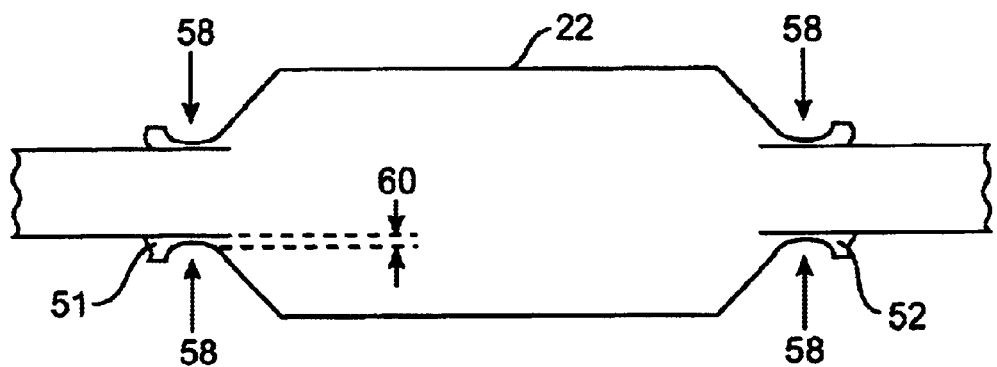
FIG. 8 illustrates an exploded view of a distal end of a cryotherapy catheter with rupture disks.

Referring now to FIG. 7, an exploded view of a distal end of the cryotherapy catheter shows that proximal 50 and distal 52 balloon stems of the first 22 and second 24 balloon are staggered along the distal end 16 of the catheter body 10. The balloons stems or bond joints 50, 52 are staggered to provide a lower balloon folding profile and to allow positioning of a vacuum port 54, which will be discussed in more detail below, between the proximal balloon stems 50 of the first and second balloons 22, 24. The balloon stems 50, 52 of the first and second balloons will be staggered from each other by a distance 56 of 5 mm or less, preferably from about 2 mm to about 3 mm. Referring now to FIG. 8, the cryotherapy catheter may further comprise at least one rupture disk 58 molded into a proximal 50 or distal 52 balloon stem of the first balloon. In some instances, the cryotherapy balloons may fail or burst on inner bond joints in a peel mode or the inner balloon may simply burst. As such, it is desirable to mold rupture discs 58 or thin spots into the balloons stems 50, 52 so that in the event of a failure, the rupture disc will allow a small amount of fluid leakage at a slow rate into a vacuum space (which is described in more detail below), allowing the cryotherapy system to shut down before the balloon bursts. Such discs 58 will reduce a stem thickness 60 to about 0.0005 inches or less.

Figure 9:
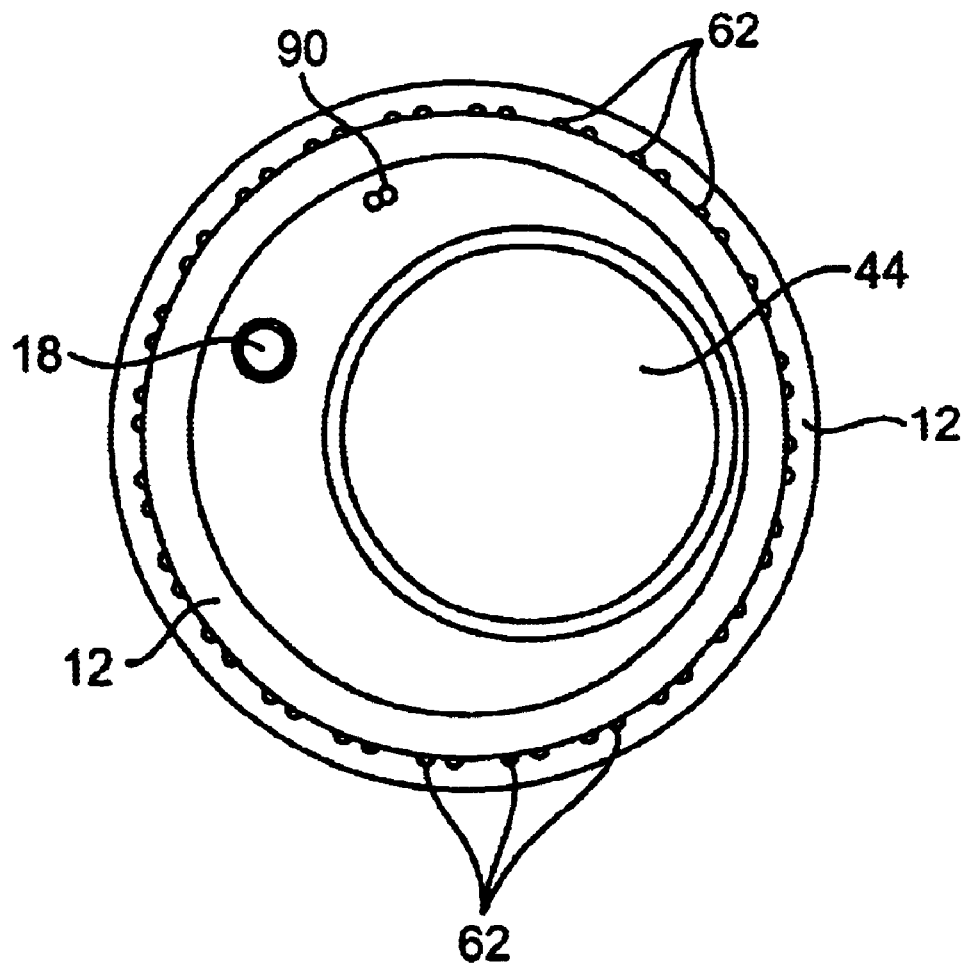
FIG. 9 illustrates a cross-sectional view of a cryotherapy catheter with multiple vacuum lumens.

The cryotherapy catheter 10 in FIG. 1 additionally illustrates several safety mechanisms that monitor the containment of the cryotherapy system. The first balloon 22 defines a volume in fluid communication with the supply 18 and exhaust 20 lumens. A fluid shutoff couples a cryogenic fluid supply with the supply lumen 18. The second balloon 24 is disposed over the first balloon 22 with a vacuum space 60 therebetween. The vacuum space 60 is coupled to the fluid shutoff by a plurality of vacuum lumens 62, as shown in FIG. 9, or optionally by a single vacuum lumen 62, as shown in FIG. 1. The fluid shutoff inhibits flow of cryogenic fluid into the first balloon 22 in response to a change in at least one of the vacuum lumens 62 and/or in response to a change in the vacuum space 60.

Figure 10:
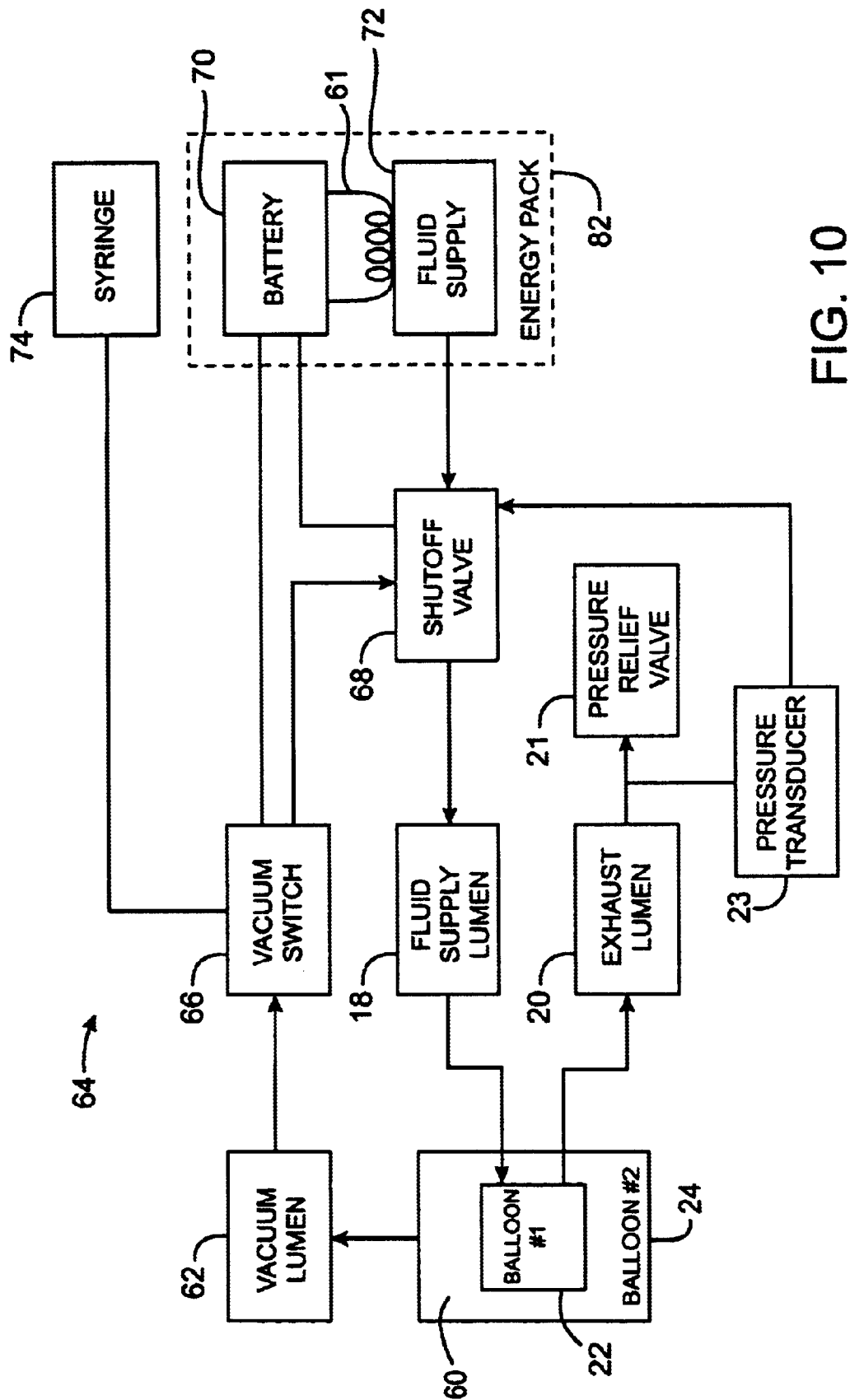
FIG. 10 is a functional flow diagram illustrating the operation of an automatic fluid shutoff mechanism of the catheter of FIG. 1.

FIG. 10 illustrates a functional flow diagram of the automatic fluid shutoff mechanism 64. The fluid shutoff 64 typically comprises a vacuum switch 66 connected to a shutoff valve 68 by a circuit, the circuit being powered by a battery 70. The switch 66 may remain closed only when a predetermined level of vacuum is detected. The closed switch 66 allows the shutoff valve 68, in fluid communication with the cryogenic fluid supply 72, to be open. Alternatively, the circuit may be arranged so that the switch 66 is open only when the predetermined vacuum is present, with the shutoff valve 68 being open when the switch is open. The vacuum is reduced when there is a breach in the catheter body 12, allowing cryogenic fluid or blood to enter at least one vacuum lumen 62, the first balloon 22 is punctured, allowing cryogenic fluid to enter the vacuum space 52, or the second balloon 24 is punctured, allowing blood to enter the vacuum space 52. In addition to monitoring the containment of both the catheter body 12 and the balloons 22, 24 during cooling, in the event of a failure, the vacuum switch 66 will be triggered to prevent the delivery of additional cryogenic fluid from the fluid supply 72 into the supply lumen 18. The second balloon 24 also acts to contain any cryogenic fluid that may have escaped the first balloon 22. The exhaust lumen 20 is fluidly connected to a pressure relief valve 21 which in turn will typically vent to atmosphere.

Figure 11:
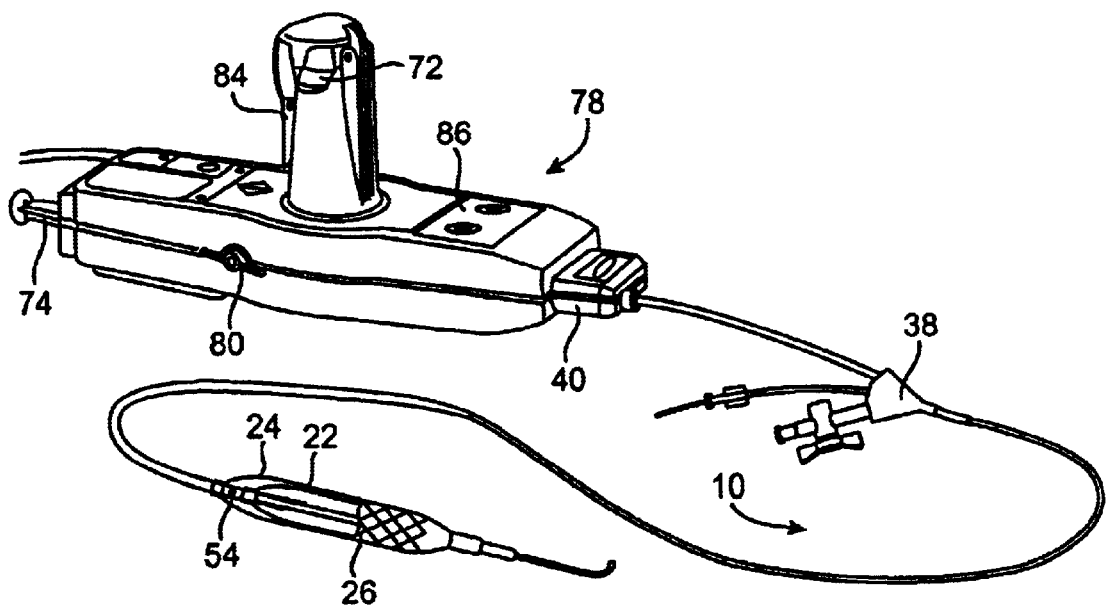
FIG. 11 illustrates a cryogenic inflation unit for use with the cryotherapy catheter of FIG. 1.

Referring now to FIG. 11, the vacuum may be provided by a positive displacement pump, such as a syringe 74, coupled to the vacuum space 60 by a plurality of vacuum lumens 62 of the body 12 via vacuum ports 76, 54. The syringe 74 is disposed within an inflation unit handle 78. A valve, such as a simple stopcock 80, may be disposed between the syringe 74 and the vacuum lumens 62 so as to isolate a relatively large syringe volume from a relatively small vacuum volume. This in turn facilitates detection of small fluid leaks, as a change in the vacuum as small as 0.2 mL may be monitored. The vacuum space 60 comprises a small volume of vacuum in the range from 1 mL to 100 mL, preferably 10 mL or less. The battery 70 may be electrically coupled to a heater 61 for heating the fluid supply 72 and cryogenic fluid therein to room temperature or warmer so as to enhance the fluid pressure and cooling system performance, as is more fully described in co-pending application Ser. No. 09/268, 205. The cryogenic fluid supply 72, battery 70 for powering the circuit, and heater 61 may be packaged together in an energy pack 82 that is detachable from the inflation unit 78 via a latch 84 and disposable. An overlay 86 of the cryo-inflation unit handle 78 is also illustrated in FIG. 11.

The fluid supply 72 will typically comprise a metallic canister or cartridge that may be transported, stored, and optionally, used at room temperature or warmer. Suitable canisters will hold quantities of cryogenic cooling fluid that are sufficient to cool the target tissue to the treatment temperature range for a time in the predetermined time range. Canisters might have volumes between 10 cc and 20 cc (depending in part on flash expansion temperatures of the cryogenic fluid), and may contain between about 8 g to about 25 g of cooling fluid. Conveniently, such canisters are commercially available for use in whipped cream dispensers. As explained above, the canister 72 may be at room temperature or even chilled, but will preferably be warmed by heater 61 prior to use. Suitable cryogenic fluids will preferably be non-toxic and may include liquid nitrous oxide, liquid carbon dioxide, cooled saline and the like. The cryogenic fluid will flow through the supply lumen 18 as a liquid at an elevated pressure and will vaporize at a lower pressure within the first balloon 22. For nitrous oxide, a delivery pressure within the supply lumen 18 will typically be in the range from 600 psi to 1000 psi at a temperature below the associated boiling point. After vaporization, the nitrous oxide gas within the first balloon 22 near its center will have a pressure typically in the range from 50 psi to 150 psi. Preferably, the nitrous oxide gas will have a pressure in the range from 75 psi to 125 psi in a peripheral artery and a range from about 75 psi to 125 psi in a coronary artery.

The mechanical strength of the vasculature generally requires quite a high pressure to dilate the vessel during conventional angioplasty. Conventional angioplasty often involves the inflation of an angioplasty balloon with a pressure of roughly 10 bar. These relatively high pressures can be safely used within the body when balloons are inflated with a benign liquid such as contrast or saline. However, high pressures involve some risk of significant injury should the balloon fail to contain a cryogenic gas or liquid/gas combination. The cooling process changes the mechanical properties of the vessel and allows it to be expanded or dilated at a much lower pressure than is used with conventional angioplasty. For example, dilation of a cryogenically cooled vessel may require inflation with a fluid pressure of about 10 bar for conventional uncooled angioplasty on the same vessel wall. Simultaneous cryogenic cooling and angioplasty may reduce and/or eliminate medial vessel fractures, thereby inhibiting proliferative response after angioplasty.

The cryotherapy catheter may additionally comprise a thermocouple 90, pressure transducer, capillary tube, thermistor, or the like coupled to the first balloon 22 to determine the pressure and/or temperature of fluid in the first balloon 22. This allows for accurate real time measurements of variables (pressure, temperature) that effect the efficacy and safety of cryotherapy treatments. Moreover, an indicator, such as a warning light or audio signal on the handle overlay 86, may additionally be coupled to the thermocouple 90 to provide a signal to an operator of the system when the first balloon temperature is above 0° C. As cryoplasty often results in adhesion of the cooling balloon to the vessel wall during treatment, an indicator lets an operator of the system know when to safely remove the cooling balloon following treatment so that any potential tearing of the vessel resulting from a frozen cooling balloon is minimized.

The cryotherapy catheter 10 in FIG. 1 may also monitor the containment of the system (i.e. catheter body 12, supply lumen 18, guidewire lumen 44, balloons 22, 24) prior to any treatment procedures. A pressure transducer 23 is coupled to the exhaust lumen 20 so as to measure a gas pulse pressure therein. The pressure transducer 23 is also coupled to the fluid shutoff valve 68 so as to inhibit flow of cryogenic fluid into the first balloon 22 if the pressure measured by the pressure transducer 23 is below 60 psi or above 80 psi. Alternatively, the fluid shutoff valve 68 may inhibit flow of cryogenic fluid into the first balloon 22 if a pressure decay measured by the pressure transducer 23 is greater than 5 psi. The pre-treatment test may be effected by introducing a short pulse of gas, typically nitrous oxide, for a fraction of a second into the first balloon 22 with the supply lumen and exhausting the gas. Containment of the supply lumen 18, balloon 22, guidewire lumen 44, and catheter body 12 are monitored by measuring a gas pulse pressure therein. In the case of a breach in the system, the system will not enter the treatment mode.

Figure 12:
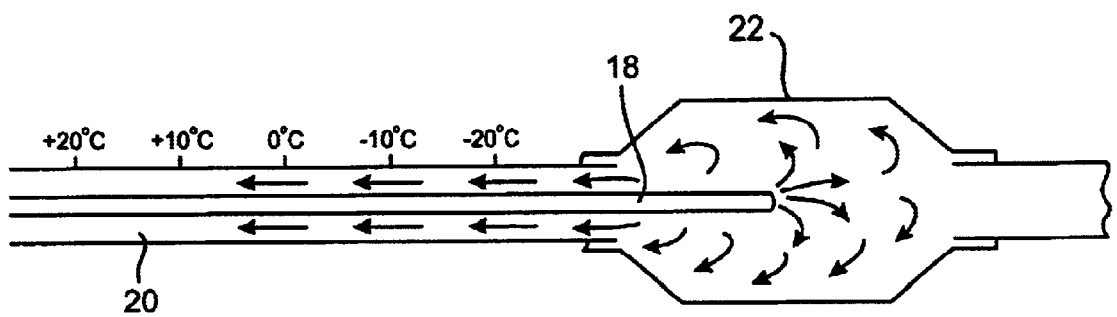
FIG. 12 illustrates a method for enhancing performance of a cryotherapy catheter.

With reference now to FIG. 12, methods for enhancing cryogenic cooling fluid flow rates in a cryotherapy system will be described. Cryogenic cooling fluid is introduced into the first balloon 22 with the supply lumen 18. The first balloon 22 is flooded so that at least some of the cooling fluid is exhausted in the balloon 22 and at least some of the cooling fluid overflows and evaporates adjacent the supply lumen 18, as depicted in FIG. 12. The supply lumen 18 and cryogenic fluid therein are cooled so as to enhance a flow rate of the cryogenic cooling fluid. Enhanced flow rates achieved from flooding the cryotherapy balloon 22 also allow the supply lumen diameter to be reduced to a range from about 0.004 inches to about 0.012 inches. Moreover, the cryotherapy system may be less dependent on canister pressure as enhanced flow rates compensate for lower cryogenic cooling fluid canister pressurizations at a range from about 600 psi to about 850 psi. Typically, the canister 72 will be heated by a heater 61 to a pressure of about 850 psi. The heater may then be additionally cycled on and off during the treatment so that the pressure of the canister 72 is maintained so that a sufficient flow of cryogenic fluid enters the first balloon 22. Such heating and cycling by the heater requires the use of an external battery. However, by flooding the first balloon 22 and cooling the supply lumen 18 and fluid therein, enhanced flow can be achieved at lower pressures. Moreover, as heat cycling is no longer necessitated with lower canister pressures, the heater can be powered with a smaller internal battery 70 that can be more easily incorporated into the inflation unit handle 78.

Figure 13A:
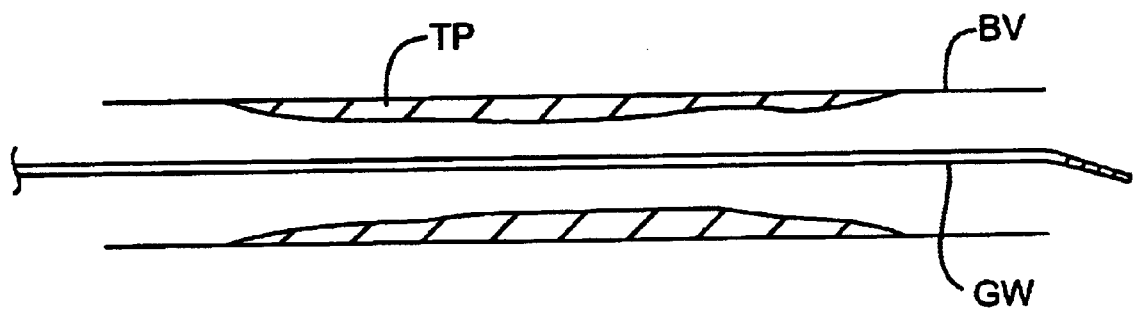
FIGS. 13A–13C schematically illustrate a method for using a cryotherapy catheter in a blood vessel.
Figure 13B:
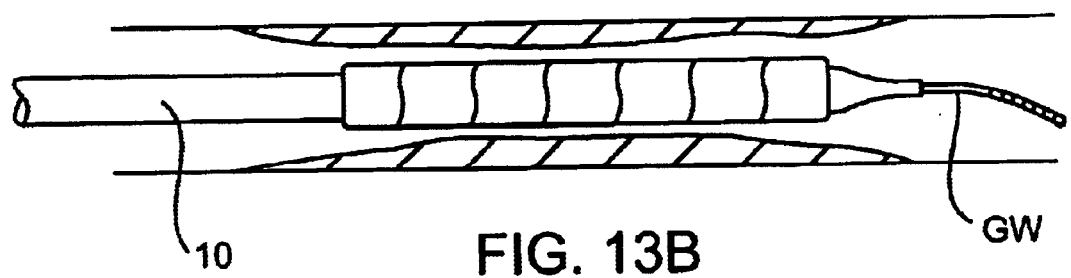
Figure 13C:
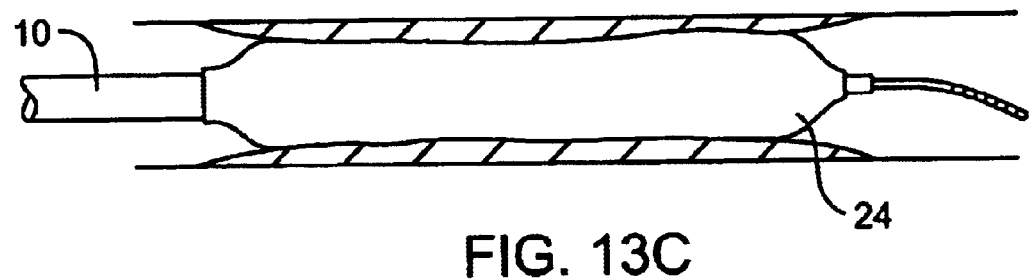

Referring now to FIGS. 13A through 13C, use of the cryotherapy catheter of FIG. 1 for treating a target portion TP within a blood vessel BV will be described. The catheter 10 is introduced over a guidewire GW, as shown in FIGS. 13A and 13B, so that the first balloon 22 is positioned within the blood vessel BV adjacent the target portion TP. Cryogenic cooling fluid is introduced into the first balloon 22 (in which it often vaporizes) and exhausted. The second balloon 24 expands to radially engage the vessel wall, as seen in FIG. 13C. The vaporized fluid serves both to inflate balloon 22 (and expand balloon 24) and to cool the exterior surface of the balloons 22, 24. The target portion is cooled to a temperature which is sufficiently low for a time which is sufficiently long to inhibit excessive cell proliferation. Heat transfer will be inhibited between the first and second balloons 22, 24 by the thermal barrier 26 so as to limit cooling of the target portion to a desired temperature profile. Moreover, containment of the catheter body 12 and balloon 22, 24 during treatment will be monitored by applying a vacuum within the space between the first and second balloons.

Generally, the temperature of the outer surface of the first balloon 22 will be in a range from about 0° C. to about −50° C. Preferably, the temperature of the outer surface of the first balloon 22 in a peripheral artery will be in a range from about 0° C. to about −40° C. The temperature of the outer surface of the second balloon 24 will be in a range from about −3° C. to about −15° C. This will provide a desired treatment temperature in a range from about −3° C. to about −15° C. The tissue is typically maintained at the desired temperature for a time period in the range from about 1 to 60 seconds, preferably being from 20 to 40 seconds. Hyperplasia inhibiting efficacy may be further enhanced by repeating cooling in cycles, typically with from about 1 to 3 cycles, with the cycles being repeated at a rate of about one cycle every 60 seconds.

Although certain preferred embodiments and methods have been disclosed herein, it will be apparent from the foregoing disclosure to those skilled in the art that variations and modification of such embodiments and methods may be made without departing from the true spirit and scope of the invention. Therefore, the above description should not be taken as limiting the scope of the invention which defined by the appended claims.

What is claimed is:

1. A cryotherapy catheter comprising:
   a catheter body having a proximal end and a distal end with a cooling fluid supply lumen and exhaust lumen extending therebetween;
   a first balloon disposed at the distal end of the catheter body, the first balloon having an inner surface in fluid communication with the supply lumen and exhaust lumen; and
   a second balloon disposed over the first balloon with a barrier therebetween.

2. A cryotherapy catheter as in claim 1, wherein the barrier comprises a separation maintained between the balloons by a polyester layer.

3. A cryotherapy catheter as in claim 2, wherein polyester layer is puncture resistant.

4. A cryotherapy catheter as in claim 2, wherein the polyester layer retains balloon folds after the balloons are expanded.

5. A cryotherapy catheter as in claim 1, wherein the barrier comprises a separation maintained between the balloons by a fluid layer.

6. A cryotherapy catheter as in claim 5, wherein the fluid layer comprises at least one liquid selected from the group consisting of propylene glycol, propylene glycol 200, propylene glycol 300, propylene glycol 400, propylene glycol 600, glycerin, ethyl alcohol 75%, ethyl alcohol 95%, dimethyl sulfoxide, glyceryl formal, N-methyl-2-pyrrolidose, tetrahydrofurfuryl, dimethyl acetamide, and monthiol glycerol.

7. A cryotherapy catheter as in claim 1, wherein the barrier is a thermal barrier.

8. A cryotherapy catheter as in claim 1, further comprising a radiopaque marker on or within the barrier.

9. A cryotherapy catheter as in claim 8, wherein the radiopaque marker has a stent-like pattern.

10. A cryotherapy catheter as in claim 9, wherein areas of the barrier adjacent balloon folds are free of the radiopaque marker.

11. A cryotherapy catheter as in claim 8, wherein the radiopaque marker comprises tungsten.

12. A cryotherapy catheter as in claim 8, wherein the radiopaque marker is conductive.

13. A cryotherapy system comprising:
    an elongate body having a proximal end and a distal end with a fluid supply lumen, an exhaust lumen, and a plurality of vacuum lumens extending therebetween;
    a first balloon defining a volume in fluid communication with the supply and exhaust lumens;
    a cryogenic fluid supply;
    a fluid shutoff coupling the cryogenic fluid supply with the supply lumen; and
    a second balloon disposed over the first balloon with a vacuum space therebetween, the vacuum space coupled to the fluid shutoff by the plurality of vacuum lumens.

14. A cryotherapy system as in claim 13, wherein the fluid shutoff inhibits flow of cryogenic fluid into the first balloon in response to a change in at least one of the vacuum lumens.

15. A cryotherapy system as in claim 13, wherein the fluid shutoff inhibits flow of cryogenic fluid into the first balloon in response to a change in the vacuum space.

16. A cryotherapy system as in claim 13, further comprising a syringe coupled to the vacuum space by the plurality of vacuum lumens.

17. A cryotherapy system as in claim 16, further comprising a valve disposed between the syringe and the vacuum lumens so as to isolate a syringe volume from a vacuum volume.

18. A cryotherapy system as in claim 17, wherein the fluid shutoff detects changes in the vacuum space of at least 0.2 mL.

19. A cryotherapy system as in claim 13, further comprising a thermocouple, pressure transducer, or capillary tube coupled to the first balloon volume to determine a temperature or pressure within the first balloon.

20. A cryotherapy system as in claim 19, further comprising an indicator coupled to the thermocouple which provides a signal when the first balloon temperature is above 0° C.

21. A cryotherapy system as in claim 13, further comprising a polyester layer marked with tungsten disposed between the first and second balloons.

22. A cryotherapy catheter comprising:
   a catheter body having a proximal end and distal end with a cooling fluid supply lumen and an exhaust lumen extending therebetween;
   a first balloon disposed at the distal end of the catheter body, the first balloon having an inner surface in fluid communication with the supply and exhaust lumens; and
   a second balloon disposed over the first balloon, wherein proximal and distal balloon stems of the first and second balloon are staggered along the distal end of the catheter body.

23. A cryotherapy catheter as in claim 22, further comprising a vacuum port positioned between the proximal balloon stems of the first and second balloons.

24. A cryotherapy catheter as in claim 22, further comprising a rupture disk molded into a proximal or distal balloon stem of the first balloon.

25. A cryotherapy catheter as in claim 22, further comprising a polyester layer marked with tungsten disposed between the first and second balloons.

26. A cryotherapy system comprising:
   a cryotherapy catheter as in claim 22;
   a cryogenic fluid supply;
   a fluid shutoff coupling the cryogenic fluid supply with the supply lumen; and
   a vacuum space between the first and second balloons, the vacuum space coupled to a fluid shutoff by a plurality of vacuum lumens.

27. A cryotherapy system comprising:
   a catheter body having a proximal end and a distal end with a cooling fluid supply lumen and an exhaust lumen extending therebetween;
   a balloon disposed at the distal end of the catheter body, the balloon having an inner surface in fluid communication with the supply lumen and exhaust lumen;
   a cryogenic fluid supply coupled to the catheter body, the cryogenic fluid supply having a gas pulse mode effecting introduction of a pulse of gas pressure into the supply lumen;
   a pressure transducer coupled to the catheter body so as to measure gas pulse pressure therein.

28. A cryotherapy system as in claim 27, further comprising:
   a fluid shutoff coupling the cryogenic cooling fluid supply with the supply lumen; and
   wherein the pressure transducer is coupled to the fluid shutoff so as to inhibit flow of cryogenic fluid into the first balloon if the pressure measured by the pressure transducer is below 60 psi or above 80 psi.

29. A cryotherapy system as in claim 27, further comprising:
   a fluid shutoff coupling the cryogenic cooling fluid supply with the supply lumen; and
   wherein the pressure transducer is coupled to the fluid shutoff so as to inhibit flow of cryogenic fluid into the first balloon if a pressure decay measured by the pressure transducer is greater than 5 psi.

30. A method for monitoring containment of a cryotherapy catheter before a cryotherapy treatment, the method comprising:
   introducing a pulse of gas into a balloon with a supply lumen;
   exhausting the gas;
   monitoring containment of the supply lumen, balloon, guidewire lumen, and catheter body by measuring a gas pulse pressure; and
   inhibiting flow of cryogenic fluid into the balloon if the measured pressure is below a threshold pressure.

31. A method for enhancing cryogenic cooling fluid flow rate in a cryotherapy system, the method comprising:
   pressurizing a cryogenic cooling fluid canister at a pressure in a range from about 600 psi to about 850 psi:
   introducing a cryogenic cooling fluid into a balloon with a supply lumen;
   flooding the balloon so that at least some of the cooling fluid is exhausted in the balloon and at least some of the cooling fluid overflows into an exhaust lumen; and
   cooling the supply lumen and cryogenic fluid therein so as to enhance a flow rate of the cryogenic cooling fluid.

32. A method as in claim 31, wherein the supply lumen has a diameter in the range from about 0.012 inches to about 0.004 inches.

33. A method for treating a blood vessel, the vessel having a mechanical strength requiring a conventional angioplasty balloon pressure for treatment by conventional angioplasty so as to effect dilation of a vessel wall, the method comprising:
   introducing a catheter into the vessel and positioning a balloon of the catheter within the vessel; and
   cooling the vessel and effecting the dilation of the vessel wall by inflating the balloon with a cooling fluid at a cooling fluid inflation pressure, the cooling fluid inflation pressure being less than the conventional angioplasty balloon pressure.

34. A method for treating a blood vessel as claimed in claim 33, the conventional angioplasty comprising inflation of an uncooled balloon to about 145 psi as required to dilate the vessel, wherein the cooling fluid inflation pressure is in a range from about 75 psi to about 125 psi.

35. A method for treating a blood vessel as claimed in claim 33, wherein the cooling fluid comprises a gas.

* * * * *